(12) United States Patent
Liu et al.

(10) Patent No.: US 9,381,494 B2
(45) Date of Patent: Jul. 5, 2016

(54) PHOTOCATALYTIC FILM STRUCTURE

(71) Applicant: Industrial Technology Research Institute, Chutung, Hsinchu (TW)

(72) Inventors: Wu-Han Liu, Hsinchu (TW); Wei-Tien Hsiao, Hsinchu (TW); Mao-Shin Liu, Hsinchu (TW); Ming-Sheng Leu, Hsinchu (TW); Cherng-Yuh Su, Hsinchu (TW); Fuh-Sheng Shieu, Hsinchu (TW); Chin-Te Lu, Hsinchu (TW)

(73) Assignee: Industrial Technology Research Institute, Chutung, Hsinchu County (TW)

( * ) Notice: Subject to any disclaimer, the term of this patent is extended or adjusted under 35 U.S.C. 154(b) by 149 days.

(21) Appl. No.: 14/248,799

(22) Filed: Apr. 9, 2014

(65) Prior Publication Data
US 2015/0182950 A1    Jul. 2, 2015

(30) Foreign Application Priority Data

Dec. 31, 2013  (TW) .............................. 102149236 A (51) Int. Cl.
| | |
|---|---|
| *B01J 23/06* | (2006.01) |
| *B01J 35/00* | (2006.01) |
| *B01J 35/02* | (2006.01) |
| *B01J 37/02* | (2006.01) |
| *B01J 37/34* | (2006.01) |
| *C23C 4/11* | (2016.01) |

(Continued)

(52) U.S. Cl.
CPC ................ *B01J 23/06* (2013.01); *B01J 35/004* (2013.01); *B01J 35/023* (2013.01); *B01J 37/023* (2013.01); *B01J 37/349* (2013.01); *C23C 4/11* (2016.01); *A61L 9/205* (2013.01); *B01J 23/50* (2013.01); *B01J 35/0013* (2013.01); *B01J 37/0225* (2013.01)

(58) Field of Classification Search
None
See application file for complete search history.

(56) References Cited

U.S. PATENT DOCUMENTS

| | | | |
|---|---|---|---|
| 6,722,159 | B2 | 4/2004 | Greenberg et al. |
| 6,939,611 | B2 | 9/2005 | Fujishima et al. |
| 7,157,840 | B2 | 1/2007 | Fujishima et al. |

(Continued)

FOREIGN PATENT DOCUMENTS

| | | |
|---|---|---|
| TW | 142396 | 9/1990 |
| TW | 544393 B | 8/2003 |
| TW | I382958 B | 1/2013 |

OTHER PUBLICATIONS

Tului et al (Optical properties of plasma sprayed ZnO+Al2O3 coatings, Surface and Coatings Tech. 179 (2004) 47-55).*

(Continued)

*Primary Examiner* — Melvin C Mayes
*Assistant Examiner* — Michael Forrest
(74) *Attorney, Agent, or Firm* — McCarter & English, LLP; Yu Lu (57) ABSTRACT

A photocatalytic film structure is provided. The photocatalytic film includes a plurality of micron particles; a plurality of nano particles; and a plurality of block bodies, wherein the volume of each of the block bodies is greater than that of each of the nano particles, and each of the micron particles, the nano particles and the block bodies contains zinc oxide and a doping metal, and wherein the amount of the doping metal is 1 to 5 wt % of the photocatalytic film, and the plurality of micron particles and micron particles take up 10 to 50% of the volume of the photocatalytic film.

9 Claims, 5 Drawing Sheets

(51) Int. Cl.
*A61L 9/20* (2006.01)
*B01J 23/50* (2006.01)

(56) References Cited

U.S. PATENT DOCUMENTS

| | | | |
|---|---|---|---|
| 7,510,765 | B2 | 3/2009 | Bujard |
| 7,597,930 | B2 | 10/2009 | Boire et al. |
| 2004/0146658 | A1* | 7/2004 | Tului ............... C23C 28/00 427/453 |
| 2010/0190633 | A1 | 7/2010 | Bai et al. |

OTHER PUBLICATIONS

Office Action issued May 5, 2015 in corresponding TW 102149236 application.
English abstract of TW 142396.
English abstract of TW 544393.
English abstract of TW I382958.
Su et al., "Evaluation of the microstructural and photocatalytic properties of aluminum-doped zinc oxide coatings deposited by plasma spraying," *Thin Solid Films*, 544:170-174 (2013).

* cited by examiner

PHOTOCATALYTIC FILM STRUCTURE

CROSS-REFERENCE TO RELATED APPLICATION

This application claims foreign priority under 35 U.S.C. §119(a) to Patent Application No. 102149236, filed on Dec. 31, 2013, in the Intellectual Property Office of Ministry of Economic Affairs, Republic of China (Taiwan, R.O.C.), the entire contents of which patent application are incorporated herein by reference.

BACKGROUND OF THE INVENTION

1. Field of the Invention

This invention relates to coating structures, and more particularly, to a photocatalytic film structure.

2. Background

Photocatalytic materials are bionic materials with self-cleaning functions, and therefore, they have now been widely used in daily life technologies. Advancement of technological developments and improvements of living standards in the recent years have drawn continuing increased attention on the safety of photocatalytic products, in addition to their effects (e.g., self-cleaning and antibacterial functions) associated daily use products.

Conventionally, photocatalytic coatings with polymeric resins, if being applied outdoors, might age in sunlight due to the presence of the polymeric resins. As such, the photocatalytic coatings cannot utilize the ultraviolet spectrum from sunlight to activate photocatalysis for achieving decontamination and deodorization.

On the other hand, as the photocatalytic coatings become rougher and have greater surface areas, the effect of photocatalysis is better. However, the photocatalytic ceramics prepared by sintering have surface atoms of the particles diffused towards the center thereof during sintering, such that the surfaces of photocatalytic coatings tend to be smooth. Hence, photocatalysis of the photocatalytic ceramics is ineffective.

Usually, the methods for immobilizing a photocatalytic material on a substrate include sol-gel methods, electrochemical deposition, chemical vapor deposition, hydrothermal methods, reaction evaporation, spraying methods, dipping, spin coating, and screen printing. For example, in a reactive evaporation, which is used to prepare a $TiO_2$ photocatalytic material, polymeric agents such as adhesives are added to increase the adhesion between materials or the adhesion between a material and a substrate. In order to remove volatile agents, heating or sintering is sometimes used to remove residual volatile agents. Further, the solidification of an adhesive is accelerated to enhance the adhesion with the substrate to form a photocatalytic film.

However, the reactive evaporation usually results in residual acidic or alkaline solutions, which would cause body damage, food contamination or environmental hazards after long-term contacts. In addition, the production of a $TiO_2$ photocatalytic film immobilized on a substrate is conducted by mainly using processes, such as immersion plating, sputtering, curtain plating, brush plating and spin plating. The adhesions of the $TiO_2$ photocatalytic films to the substrates prepared by the above methods are poor, such that the films are easily peeled off upon the application of an external force.

A photocatalytic film produced by physical vapor deposition or chemical vapor deposition is relatively thin, i.e., about 1 micron or smaller. Ultraviolet rays might directly penetrate through the photocatalytic film, such that light scattering and absorption cannot take place uniformly on the film. The small overall surface area of the film makes the effect of its photocatalytic treatment of external organic contaminants poor. Moreover, since the photocatalytic film is too thin to sufficiently endure an outdoor environment (e.g., on outdoor walls or bridge surfaces) which abrades and harms the film in the long-term, the rapid erosion and disappearance of the film often happen at those areas, and thereby losing the original photocatalytic properties of the film.

Accordingly, the present disclosure provides a photocatalytic film structure which can resolve the above issues.

SUMMARY OF THE INVENTION

A photocatalytic film structure including a plurality of micron particles; a plurality of nano particles; and a plurality of block bodies is provided. The volume of each of the block bodies is greater than that of each of the nano particles. Each of the micron particles, the nano particles and the block bodies contains zinc oxide and a doping metal, wherein an amount of the doping metal is 1 to 5 wt % of the photocatalytic film, and the plurality of micron particles and micron particles take up 10 to 50% of the volume of the photocatalytic film.

DETAILED DESCRIPTION OF THE INVENTION

The detailed description of the invention is illustrated by the specific embodiments below, so as to allow a person skilled in the art to easily appreciate the other advantages and effects of the disclosure of the present specification.

In the present disclosure, a photocatalytic raw material in a molten state or a semi-molten state is sprayed on a substrate under a high pressure by thermal spraying. During this process, the photocatalytic raw material first was heated by steam gas and/or then was impacted on a surface of the substrate. The phenomenon causes the explosion of some of the photocatalytic raw material and consequently forms irregularly globular or non-globular particles, so as to effectively bind to the photocatalytic raw material in a molten state or a semi-molten state subsequently sprayed on the surface of the substrate, and thereby increasing the efficiency of the adhesion of the photocatalytic raw material to the surface of the substrate.

Specifically, the photocatalytic film structure of the present disclosure is formed by thermal spraying. During the travel of the photocatalytic raw material following by jet steam gas, they will frequently contact each other on the surface of substrate, and then the micron particles and nano particles significantly yielded by the consequences of explosion behavior. The explosion behavior results from the strong thermal expansion of the raw material. During the subsequent spraying of the photocatalytic raw material on the surface of the substrate, the micron particles and nano particles in a molten state, which are formed by disintegrating the photocatalytic raw material, adhere to one another to form block bodies with larger particle diameters. These micron particles and the flattened block bodies play a role in bonding the substrate and the nano particles, and form a higher bonding strength on a substrate bonding surface as compared with a conventional brush coating method or a adhesive/binder agent method (such as bonding a photocatalytic cardboard, a plastic board or a metal board).

The photocatalytic raw material of the present disclosure has a hollow structure, such that the material can be heated to swell during thermal spraying. Later, during the traveling of the material to the substrate by spraying, the material disintegrates by exploding or collapsing to form a plurality of nano and micron particles, which may be globular or non-globular in shape.

The present disclosure provides a photocatalytic film structure that includes a plurality of micron particles; a plurality of nano particles; and a plurality of block bodies. The volume of each of the block bodies is greater than that of each of the nano particles, wherein each of the micron particles, nano particles and block bodies contains zinc oxide and a doping metal.

The amount of the doping metal takes up 1 to 5 wt % of the photocatalytic film structure, and the plurality of the micron particles and nano particles take up 10 to 50% of the volume of the photocatalytic film structure.

In one embodiment, the plurality of micron particles have a particle diameter ranging from 5 to 45 μm. The plurality of the nano particles have a particle diameter ranging from 95 to 195 nm.

In one embodiment, the sizes of some of the block bodies in a direction parallel to the surface of the substrate are greater than the sizes in a direction perpendicular to the surface of the substrate.

In the present disclosure, the micron particles, nano particles and block bodies adhere to each other. Specifically, the micron particles, nano particles and block bodies are molten or semi-molten to adhere to each other.

The photocatalytic film structure of the present disclosure has a thickness ranging from 20 to 70 μm.

The photocatalytic film structure of the present disclosure has porosity ranging from 1 to 20%.

In one embodiment, the doping metal is at least one selected from the group consisting of Al and Ag.

In one embodiment, zinc oxide takes up 95 to 99 wt % of the photocatalytic film structure, and the doping metal is located in the crystal lattice structure of zinc oxide.

In one embodiment, the photocatalytic film structure is formed on a substrate, wherein the substrate may be a metal, an alloy, ceramics or glass.

In another embodiment, the substrate is glass, and the surface of the glass is in a semi-molten state to adhere to the photocatalytic film structure.

Example 1

Preparation of a Photocatalytic Film Structure of the Present Disclosure

First, the substrates used in this example were stainless (SS304), aluminum and glass substrates, each of which had a size of L120×W25×t3 mm$^3$. A thermal sprayer (A3000, F4 gun) was used under a mixed gas environment composed of an argon gas at a rate of 41 liters per minute and a hydrogen gas at a rate of 8 to 14 liters per minute, along with a plasma spraying gun with an inlet diameter of 6 mm, a voltage of 530 to 630 amperes, at a spraying distance of 110 to 140 mm and the use of 3.5 liters of an argon gas per minute as a carrier gas, and a photocatalytic raw material (purchased from Yong-Zhen Technomaterial CO., LTD, QF-ZNA-97) was delivered at a rate of 10 to 12 grams per minute and sprayed on the area (i.e., L120×W25 mm$^2$) of each of the test pieces by going back and forth on the test pieces for scanning 20 times. The photocatalytic film structures of the present disclosure were then obtained. It was found that the photocatalytic film structures were intact, and firmly formed on the stainless (SS304), aluminum, and glass substrates.

Figure 1A:
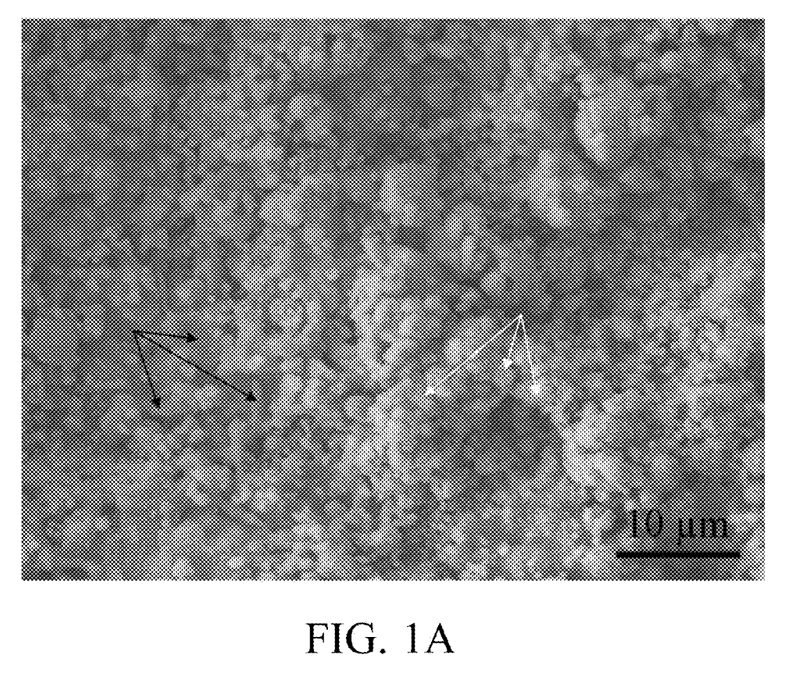
FIG. 1A shows the appearance of a photocatalytic film structure prepared in Example 1 under a scanning electronic microscope (SEM) at a magnification of 2000×, and the black arrows in FIG. 1A indicate a plurality of micron particles, and the white arrows indicate a plurality of nano particles; however

Moreover, a scanning electron microscope (SEM) at a magnification of 2000× was used to observe the appearance of the photocatalytic film structure prepared in Example 1, as shown in FIG. 1A. In FIG. 1A, the black arrows indicate a plurality of micron particles, and the white arrows indicate a plurality of nano particles. It appears that the plurality of nano particles were formed on the exploding or collapsing area related in SEM figure, and the nano particles were bonded to the micron particles.

Figure 1B:
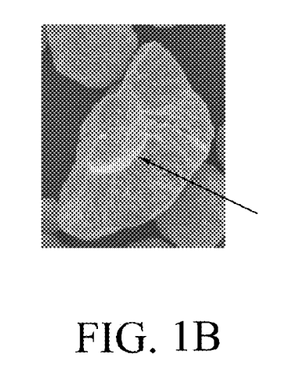
FIG. 1B shows a partial enlargement view of a particle of the photocatalytic raw material structure, and as indicated by the arrow, the shell of the particle is hollow inside.

Please refer to FIG. 1B. FIG. 1B is a partial enlargement view of a particle of the photocatalytic raw material structure. As indicated by the arrows, the shell of the particle has a hollow inside. As shown in FIGS. 1 and 1', one of ordinary skill in the art can conceive that the originally delivered photocatalytic raw material powder was only powder size at micron levels. This example did not deliver raw powder with mixed micron and nano sizes, mixed sub-micron and nano sizes or only nano sizes to prepare a nano-sized photocatalytic film like the conventional method. Instead, this example prepared a photocatalytic film structure having a plurality of micron particles, a plurality of nano particles and a plurality of block bodies which are formed by thermal spraying the powder.

Figure 2A:
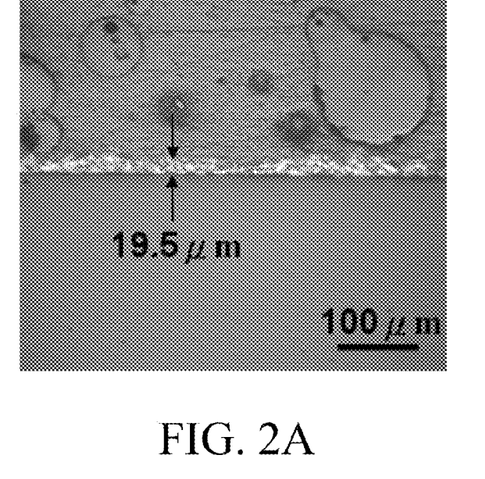
FIGS. 2A-2C show optical microscopic images for cross-sections of the photocatalytic film structures of the present disclosure with different thicknesses.
Figure 2B:
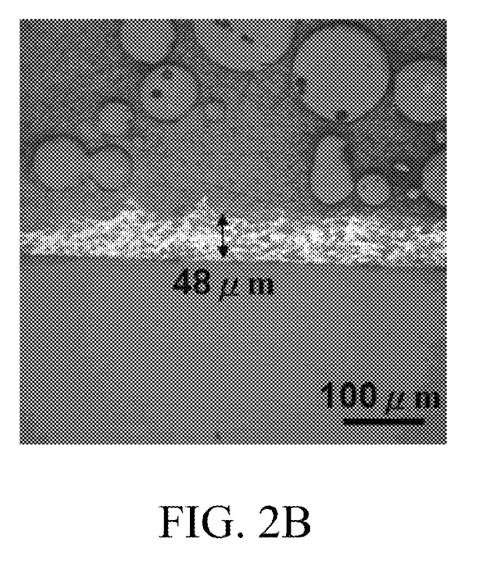
Figure 2C:
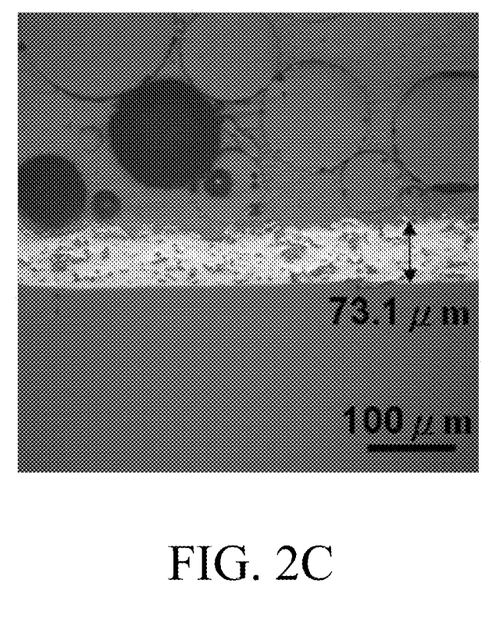

Please refer to FIGS. 2A to 2C. FIGS. 2A to 2C disclose optical microscopic images of the cross-sections of the photocatalytic film structures with different thicknesses. The photocatalytic film structure in each of the figures was prepared by using the method in Example 1 and spraying the photocatalytic raw material on a glass substrate. Moreover, when the thickness of the photocatalytic film structure was from 20 to 70 μm, it had a specific photocatalytic efficiency for the degradation of methylene blue. When the thickness was around 20 μm, for example 19.5 μm, the photocatalytic film structure had a photocatalytic efficiency of 70%. When the thickness was around 70 μm, the photocatalytic film structure had a photocatalytic efficiency of lower than 60%. When the thickness of the photocatalytic film structure was 40 to 60 μm, the highest photocatalytic efficiency was observed, i.e., higher than 70%. On the other hand, if the photocatalytic film structure was too thin, it would be disadvantageous for use in an environment where abrasion is frequent. Further, the thicker the film structure was, the lower the efficiency and the higher the production cost were.

Figure 3:
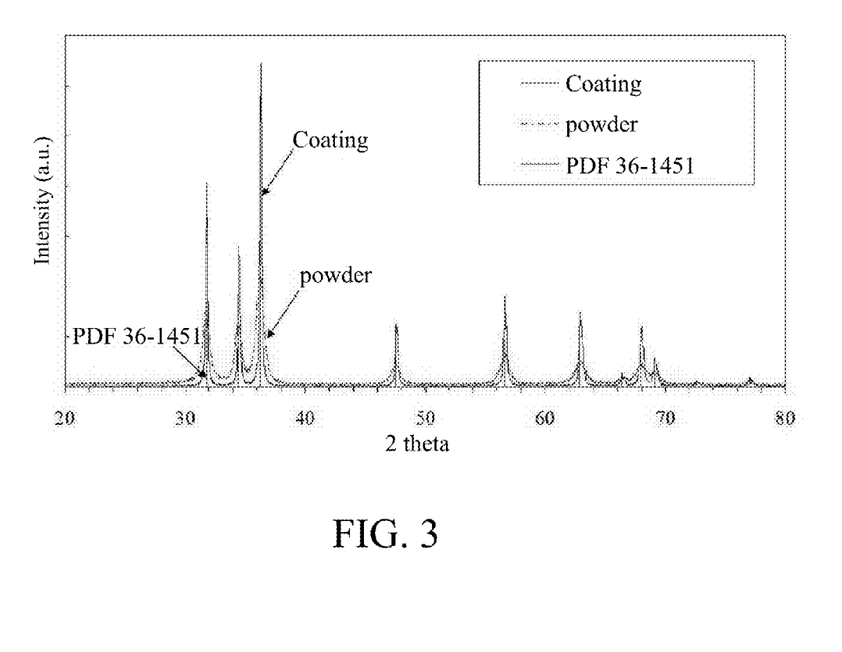
FIG. 3 shows a spectrum of an X-ray diffraction analysis on the photocatalytic structure of the present disclosure.

Furthermore, please refer to FIG. 3. As shown in the results of the X-ray diffraction analysis (XRD), the photocatalytic film structure of the present disclosure was still the standard zinc oxide (ZnO) phase (PDF36-1451). It is clear that in the present disclosure, the inherent phase of the photocatalytic raw material was not affected or altered after a plated film was formed by thermal spraying.

Example 2

Preparation of a Photocatalytic Film Structure of the Present Disclosure

First, the substrate used in this example was a stainless (SS304) substrate that had a size of L120×W25×t3 mm$^3$. A thermal spray equipment (Model J-3 spraywelder) was used under a mixed gas environment composed of cold air delivered at a pressure of 20 to 25 Psi, an oxygen gas (43% flow) delivered at a pressure of 17 Psi, and acetylene ($C_2H_2$) delivered at a pressure of 15 Psi, along with a flame spraying gun with an inlet diameter of 6 mm, at a spraying distance of 220 to 230 mm, to spray the photocatalytic raw material on the area (i.e., L120×W25 mm$^2$) of the test piece by going back and forth on the test piece for scanning 10 to 12 times. The photocatalytic film structure of the present disclosure was then obtained. Similarly, the photocatalytic film structure was intact, and firmly formed on the stainless substrate In the present disclosure, the carrier gas for delivering the photocatalytic raw material was not particularly limited. The carrier gases to be used include, but are not limited to $N_2$, $CO_2$ or $CH_4$, so as to increase the contents of the non-metal elements, such as C, H or N. In addition, when the substrate used in the present disclosure was glass, the surface of the glass substrate was a semi-molten, so as to adhere to the photocatalytic film structure.

As compared with the conventional AZO grown into elongated fibrils or existing in a polygonal morphology, it is not suitable to be delivered by thermal spray equipment. However, the photocatalytic film raw materials having relatively larger globular particles ranging from 5 to 45 microns were used for the photocatalytic film structure of the present disclosure and the particles could form flattened particles by melting or semi-melting. These flattened particles were at micron levels, and played a role in binding the substrate and nano particles together to form a higher bonding strength on a substrate bonding surface as compared with a conventional brush coating method or a adhesive/binder agent method (such as bonding a photocatalytic cardboard, a plastic board or a metal board). In addition, during the traveling of the material to the substrate by spraying, the material disintegrated by exploding or collapsing to form a plurality of nano and micron particles, which may be globular or non-globular in shape. The micron and nano particles subsequently bonded on the substrate formed block bodies with larger sizes since they melted to each other. As such, the photocatalytic film structure of the present disclosure obtained had the nano particles, micron particles and block bodies.

Figure 4:
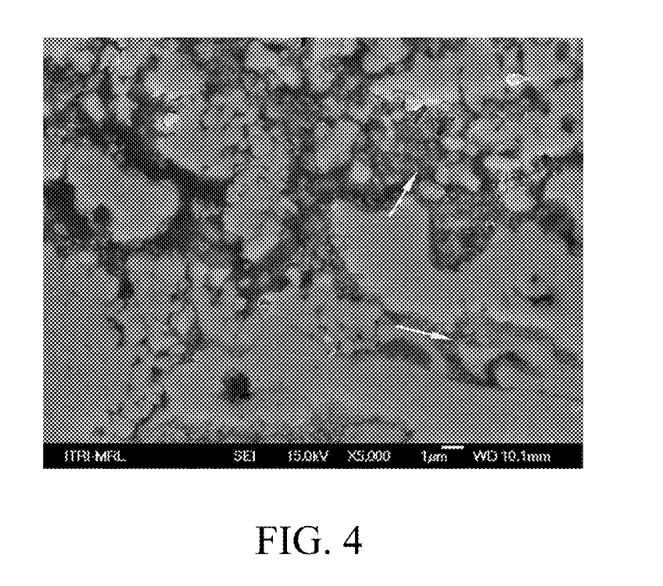
FIG. 4 shows an electron microscopic image for the cross-section of the photocatalytic film structure of the present disclosure.

FIG. 4 is an electron microscopic image for the metallograph of the cross-section of the photocatalytic structure of the present disclosure. FIG. 4 can further illustrate the features of the photocatalytic film structure. The flattened block bodies (as indicated by the enlarged gray block bodies in the figure) are responsible for adhering to each other and connecting in series to the surface of the substrate. The nano particle clusters (as indicated by the white arrows) are distributed in the pores of the coating. When the surface of the photocatalytic film was abraded, new photocatalytic nano particles with large surface areas would be exposed to impart further degradation of organic contaminants.

In addition, the bonding level of between the photocatalytic material and the substrate might be increased by a conventional brush coating method coupled with sintering. However, as compared with the process used in the present disclosure, sintering needs to be conducted at a higher temperature for long time and this long-term heat treatment process would damage those nano particles in a photocatalytic film which probably produce better photocatalytic effect. That is, sintering might make the nano particles grow into micron particles and fail to provide the photocatalytic film structure of the present disclosure, produced by thermal spraying. The photocatalytic film structure had splat particles, and the splat particles were subsequently stacked up to form flattened particles along with a hybrid structure of nano particles overlaying micron particles.

Comparative Example 1

A Photocatalytic Film Formed by Arc Ion Plating (AIP)

AIP was used to plate a doped zinc oxide (AZO) film with a thickness of less than 1 μm.

Test Example

Energy Dispersive X-Ray (EDX) Analysis

An EDX analyzer (JEOL; JSM-6500F) was used to conduct measurements. Results are recorded in Table 1. The measured spectrum is shown in FIG. 5.

TABLE 1

| Results of the EDX Analysis | | |
|---|---|---|
| | | Example 1 |
| Elemental Contents | Zn | 73.71 |
| | O | 25.03 |
| | Al | 1.26 |

Figure 5:
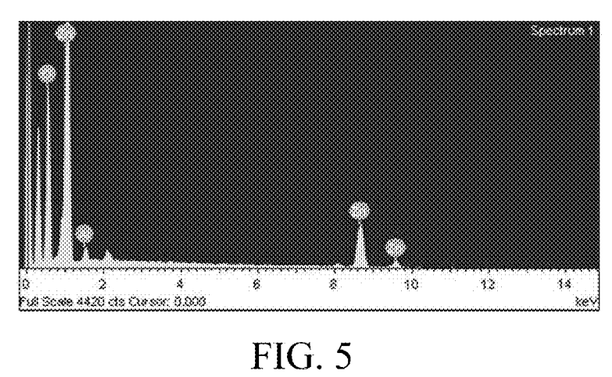
FIG. 5 shows a spectrum of an energy dispersion analysis on the photocatalytic film structure of the present disclosure.

Please refer to FIGS. 1 and 5, according to the results of the EDX analysis in Table 1, it can be seen that the proportion of the elemental contents of the photocatalytic film structure of the present disclosure was very close to the proportion of the ideal photocatalytic composition having the weight percentages of Zn, O and Al being 77.93 wt %, 20.48 wt % and 1.59 wt %, respectively. In other words, the photocatalytic film structure of the present disclosure still had the inherent zinc oxide (ZnO) phase. Further, the photocatalytic film structure of the present disclosure was not altered or damaged during thermal spraying.

Photocatalytic Effect:

An illumination experiment was conducted according to the detection method employed in the publication, *Journal of the Electrochemical Society*, 153, 10, F237-F243, 2006 and the changes on absorbance were measured.

Figure 6:
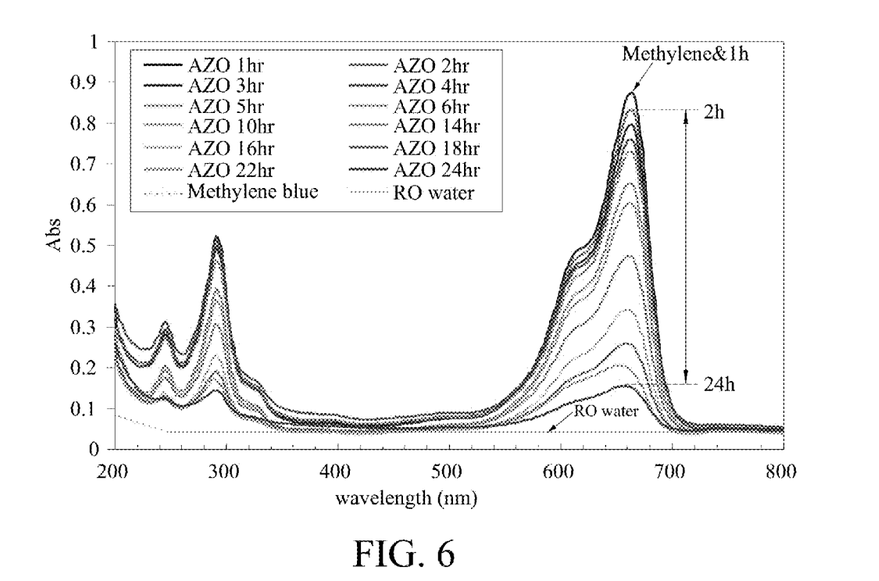
FIG. 6 shows an absorption spectrum at various time points of an illumination experiment.

The photocatalytic raw material was formed on a 2.5×2.5 cm$^2$ glass by the method in Example 1. The obtained photocatalytic film structure test piece was placed in one glass dish. The test piece was then immersed in a methylene blue solution at a concentration of $1\times10^{-5}$M in the glass dish. The test piece in the glass dish was illuminated by an UV light source with a wavelength of 365 nm and illumination intensity of 1045±40 μW/cm$^2$ in a closed chamber for blocking an external light source. The absorbances of the test piece after reacting with the methylene blue solution were analyzed with an UV-Vis spectrometer at the $1^{st}$, $2^{nd}$, $3^{rd}$, $4^{th}$, $5^{th}$, $6^{th}$, $10^{th}$, $14^{th}$, $16^{th}$, $18^{th}$, $22^{nd}$, and $24^{th}$ hours. Results are shown in FIG. 6. Moreover, after illumination on the photocatalytic film structure for 24 hours, the color of the methylene blue solution faded to become as transparent as reverse osmosis water, and the absorbance at the wavelength ranging from 600 to 700 nm was significantly reduced. This means that a photocatalytic effect indeed existed.

Furthermore, the following illustration is based on the calculated concentration of the methylene blue solution. The concentration of the methylene blue solution used for the photocatalytic film in Comparative Example 1 was recorded after 12 hours, and no significant change was found. However, when the experiment was conducted on the photocatalytic film structure formed in Example 1 and on the commercially available titanium dioxide film, it was found that the concentrations of the methylene blue solution could be reduced to $0.40 \times 10^{-5}$ M. When the time of recording was extended to the $45^{th}$ hour, the detected concentration of the methylene blue solution for the commercially available titanium dioxide film was reduced to about $0.12 \times 10^{-5}$ M. However, the detected concentration of the methylene blue solution for the photocatalytic film structure of the present disclosure was reduced to about $0.04 \times 10^{-5}$ M, indicating that the photocatalytic film structure of the present disclosure had an excellent and long-term photocatalytic effect.

In addition, the conductive properties of the photocatalytic films of Comparative Example 1 and Example 1 were confirmed by a multimeter prior to conducting the test for the photocatalytic effect. However, after 12 hours of the photocatalytic reaction, the film of Comparative Example 1 partially peeled off, and no longer had the conductive property as measured by the multimeter. Different from Comparative Example 1, the photocatalytic film structure of the present disclosure was still intact and had the conductive property after 12 hours of the photocatalytic reaction.

Detection of Antibacterial Effects:

An antibacterial experiment was conduced according to the regulation set forth in CNS 15353, at the wavelength of 543 nm, and under the illuminating condition of 1500 lux. A *Staphylococcus aureus* (BCRC 10451) liquid was added on the photocatalytic film structure test piece. After 24 hours of light and dark incubations, the colony forming units (CFU) of *S. aureus* were calculated. Results are recorded in Table 2.

TABLE 2

| | Antibacterial Effects | | |
|---|---|---|---|
| | Rinsing after Inoculation (CFU/piece) | Bacterial Density after 24 hours under the Light Condition (CFU/piece) | Bacterial Density after 24 hours under the Dark Condition (CFU/piece) |
| Blank | $6.37 \times 10^3$ | $3.17 \times 10^4$ | $4.17 \times 10^4$ |
| Example 1 | $6.37 \times 10^3$ | <10 | <10 |

According to the data in Table 2, the photocatalytic film of Example 1, when the bacterial strain adhered to, was effective in preventing the formation of bacterial colonies. Hence, the photocatalytic film of the Example 1 had an excellent antibacterial effect.

Tensile Rupture Strength:

A tensile rupture experiment was conducted by using a PAT adhesion tester (GM01, DFD Instruments) and in accordance with the ASTM C633 standard, and test pieces were adhered on the surface of a steel dolly with a diameter of 8.16 mm by using an adhesive, Plasma tex KLEBBI (manufactured by Sulzer Metco). The test pieces were the photocatalytic film structures formed by using the photocatalytic raw material and common zinc oxide powder, respectively, according to the method of Example 2. Each of the test pieces was measured three times, and an average value was calculated therefrom as the value for the tensile rupture experiment.

The results showed that the intensity value of the zinc oxide photocatalytic film structure was only 21.2 MPa, whereas the intensity value of the photocatalytic film structure of the present disclosure was up to 50.8 MPa. Hence, the photocatalytic film structure of the present disclosure indeed had excellent adhesion.

In light of the above, the present disclosure involves spraying the photocatalytic raw material in a molten or semi-molten state on a substrate by thermal spraying, exploding or collapsing the photocatalytic raw material under a heated environment to form nano and micron particles with roughly globular or globular shapes, adhering the nano particles to the roughly globular or globular micron particles, delivering the traveling particles in a molten or semi-molten state by using a carrier gas, sequentially stacking the particles on the substrate, repeatedly spraying and injecting the particles back and forth on the substrate to adjust the coating to a desired thickness, and obtaining the photocatalytic film structure of the present disclosure having a hybrid structure of the nano particles overlaying the micron particles.

In the present disclosure, during the spraying, the micron particles in the photocatalytic raw material first impacted on the substrate have become a molten or semi-molten state, and thereby forming flattened particles. These flattened particles are at micron levels. The flattened particles play a role in bonding the substrate and the nano particles, and form a higher bonding strength on a substrate bonding surface as compared with a conventional brush coating method or a adhesive/binder agent method (such as bonding a photocatalytic cardboard, a plastic board or a metal board). Moreover, the nano and micron particles subsequently bonded on the substrate generate block bodies with larger sizes since they melt to each other, so that the photocatalytic film structure of the present disclosure has the nano particles, the micron particles and the block bodies at the same time. Specifically, the photocatalytic raw material of the present disclosure is subjected to a thermal spraying process to generate a material in a thermally molten state. The pushing force exerted by a highly pressurized air or by jet stream gas sprays the molten material on the surface of a workpiece, and thereby enhancing the adhesion of the film.

The above examples are only used to illustrate the principle of the present disclosure and the effect thereof, and should not be construed as to limit the present disclosure. The above examples can all be modified and altered by those skilled in the art, without departing from the spirit and scope of the present disclosure as defined in the following appended claims.

What is claimed is:

1. A photocatalytic film structure, comprising:
   a plurality of micron particles;
   a plurality of nano particles; and
   a plurality of block bodies,
   wherein a volume of each of the block bodies is greater than that of each of the nano particles; each of the micron particles, the nano particles and the block bodies contains zinc oxide and a doping metal;
   an amount of the doping metal is 1 to 5 wt % of the photocatalytic film structure; and
   the plurality of micron particles and the plurality of nano particles take up 10 to 50% of the volume of the photocatalytic film structure, and
   wherein the photocatalytic film structure has a thickness ranging from 20 to 70 μm.

2. The photocatalytic film structure of claim 1, wherein the plurality of micron particles have a particle diameter ranging from 5 to 45 µm.

3. The photocatalytic film structure of claim 1, wherein the plurality of nano particles have a particle diameter ranging from 95 to 195 nm.

4. The photocatalytic film structure of claim 1, which has porosity ranging from 1 to 20%.

5. The photocatalytic film structure of claim 1, wherein the doping metal is at least one element selected from the group consisting of Al and Ag.

6. The photocatalytic film structure of claim 1, wherein the zinc oxide takes up 95 to 99 wt % of the photocatalytic film structure.

7. The photocatalytic film structure of claim 1, which is formed on a substrate.

8. The photocatalytic film structure of claim 7, wherein the substrate is one selected from the group consisting of a metal, an alloy, ceramics and glass.

9. The photocatalytic film structure of claim 7, wherein the sizes of some of the block bodies in a direction parallel to a surface of the substrate are greater than the sizes in a direction perpendicular to the surface of the substrate.

* * * * *